(12) United States Patent
Xu et al.

(10) Patent No.: US 12,318,554 B2
(45) Date of Patent: Jun. 3, 2025

(54) FEMORAL ARTERY CANNULA FOR PROVIDING LOWER LIMB BLOOD PERFUSION

(71) Applicant: NANJING DRUM TOWER HOSPITAL, Jiangsu (CN)

(72) Inventors: Can Xu, Jiangsu (CN); Dongjin Wang, Jiangsu (CN)

(73) Assignee: NANJING DRUM TOWER HOSPITAL, Jiangsu (CN)

( * ) Notice: Subject to any disclaimer, the term of this patent is extended or adjusted under 35 U.S.C. 154(b) by 0 days.

(21) Appl. No.: 18/862,350

(22) PCT Filed: Oct. 31, 2023

(86) PCT No.: PCT/CN2023/128165
§ 371 (c)(1),
(2) Date: Nov. 1, 2024

(87) PCT Pub. No.: WO2024/159834
PCT Pub. Date: Aug. 8, 2024

(65) Prior Publication Data
US 2025/0114561 A1    Apr. 10, 2025

(30) Foreign Application Priority Data
Feb. 3, 2023    (CN) .......................... 202320106021.6

(51) Int. Cl.
*A61M 25/00*    (2006.01)
*A61M 39/22*    (2006.01)

(52) U.S. Cl.
CPC ... *A61M 25/003* (2013.01); *A61M 2025/0031* (2013.01); *A61M 2202/0007* (2013.01);
(Continued)

(58) Field of Classification Search
CPC ............ A61M 25/003; A61M 25/0031; A61M 25/0097; A61M 2025/0039; A61M 39/10;
(Continued)

(56) References Cited

U.S. PATENT DOCUMENTS 5,931,801 A * 8/1999 Burbank ............. A61M 1/3653
604/4.01
2021/0060327 A1 * 3/2021 Singleton .......... A61M 39/0247

FOREIGN PATENT DOCUMENTS

CN    201026340 Y    2/2008
CN    205586012 U *  9/2016
(Continued)

*Primary Examiner* — Laura A Bouchelle
(74) *Attorney, Agent, or Firm* — Muncy, Geissler, Olds & Lowe, P.C.

(57) ABSTRACT

A femoral artery cannula for providing lower limb blood perfusion includes an outer tube and an inner tube. The inner tube is fixedly nested inside the outer tube, a lower surface of the outer tube is provided with a plurality of through holes, upper surfaces of outer sides of the outer tube and the inner tube are each provided with a through slot, two ends of lower sides of the two through slots are each fixedly provided with a sliding rod, a sliding plate is connected between the two sliding rods in a movably adjustable manner, a liquid injection tube is fixedly nested in an inner side of the sliding plate, lower sides of the two sliding plates are each provided with a transmission mechanism for pushing the liquid injection tubes to move, and outer sides of the through slots are each provided with a blocking mechanism.

7 Claims, 4 Drawing Sheets

(52) U.S. Cl.
CPC ............ *A61M 2202/0413* (2013.01); *A61M 2205/0205* (2013.01); *A61M 2210/086* (2013.01)

(58) Field of Classification Search
CPC ........ A61M 2039/1066; A61M 1/3621; A61M 1/3653; A61M 1/3666
See application file for complete search history.

(56) References Cited

FOREIGN PATENT DOCUMENTS

| | | | |
|---|---|---|---|
| CN | 205814842 U | 12/2016 | |
| CN | 112915294 A | 6/2021 | |
| CN | 113082452 A | 7/2021 | |
| CN | 214911437 U | 11/2021 | |
| CN | 114224041 A | 3/2022 | |
| KR | 20190091244 A | 8/2019 | |
| WO | WO-9735629 A1 * | 10/1997 | ........ A61M 25/0026 |
| WO | WO2020176968 A1 | 9/2020 | |

* cited by examiner

FEMORAL ARTERY CANNULA FOR PROVIDING LOWER LIMB BLOOD PERFUSION

TECHNICAL FIELD

The present invention relates to the technical field of medical devices, and in particular, to a femoral artery cannula for providing lower limb blood perfusion.

BACKGROUND

A femoral artery cannula may block the blood flow of the femoral artery perfusion to the lower limbs, resulting in lower limb ischemia, and even amputation in severe ischemia.

Patent no. CN 214911437 U discloses a VA-ECMO femoral artery cannula for providing lower limb blood perfusion, including a cannula body and a puncture guide core, a main cavity and a side cavity independent of each other being formed in the cannula body, the main cavity being a front-back through structure, an outer edge of a front end of the main cavity being provided with a main cavity side hole, the side cavity being wrapped around a periphery of a rear end portion of the main cavity, an outer edge of the side cavity being provided with a side cavity side hole along a same front-back straight line, an annular airbag being arranged on the cannula body at a position between the main cavity side hole and the side cavity side hole, a bulging airbag being provided at an extension line of a rear end of the side cavity side hole, and both the annular airbag and the bulging airbag being connected to airbag ports for inflation and deflation. There are still defects in this technical solution:

In the technical solution, the liquid injection tube is directly exposed to the outside and is apt to being contaminated with bacteria during storage, and as a result, causing infection of injected blood during liquid injection.

SUMMARY

An objective of the present invention is to provide a femoral artery cannula for providing lower limb blood perfusion, to solve the problem that the liquid injection tube in the VA-ECMO femoral artery cannula for providing lower limb blood perfusion in the prior art is directly exposed to the outside and is apt to being contaminated with bacteria during storage, and as a result, causing infection of injected blood during liquid injection.

To implement the foregoing objective, the present invention adopts the following technical solution.

A femoral artery cannula for providing lower limb blood perfusion includes an outer tube and an inner tube. The inner tube is fixedly nested inside the outer tube, a lower surface of the outer tube is provided with a plurality of through holes, upper surfaces of outer sides of the outer tube and the inner tube are each provided with a through slot, two ends of lower sides of the two through slots are each fixedly provided with a sliding rod, a sliding plate is connected between the two sliding rods in a movably adjustable manner, a liquid injection tube is fixedly nested in an inner side of the sliding plate, lower sides of the two sliding plates are each provided with a transmission mechanism for pushing the liquid injection tubes to move, and outer sides of the through slots are each provided with a blocking mechanism.

Preferably, the transmission mechanism includes a rotary rod and a cam, the rotary rod is arranged on the lower side of the sliding plate, two ends of the rotary rods are rotatably connected to side walls of the corresponding outer tube and inner tube through sealed bearings, the cam is fixedly nested on an outer wall of the rotary rod, the cam abuts against a lower surface of the sliding plate, one ends of the two rotary rods respectively extend to outer sides of the corresponding outer tube and inner tube and are each fixedly nested with a worm wheel, one side of the worm wheel is meshed with a worm, two ends of the worm are each rotatably connected to a side plate, and the plurality of side plates are respectively fixedly connected to outer walls of the corresponding outer tube and inner tube.

Preferably, the blocking mechanism includes a blocking plate and an engaging block, the blocking plate is arranged against the outer side of the through slot, one ends of the two blocking plates are fixedly connected to outer walls of the corresponding outer tube and inner tube through connecting strips, the engaging block is fixedly arranged on an end of the corresponding blocking plate away from the connecting strip, and the outer walls of the outer tube and the inner tube close to the engaging blocks are each provided with an engaging slot, and the engaging blocks are engaged with the corresponding engaging slots.

Preferably, rod walls of the plurality of sliding rods are all movably nested with springs, and two ends of the plurality of springs are fixedly connected to the corresponding sliding plates and outer walls of the outer tube and inner tube, respectively.

Preferably, lower ends of the plurality of sliding rods are each fixedly provided with a stopper. Preferably, one ends of the two worms are each fixedly nested with a rotary wheel.

Preferably, the blocking plates, the connecting strips, and the engaging blocks are all made of an antibacterial silica gel material.

Compared with the prior art, the present invention provides a femoral artery cannula for providing lower limb blood perfusion, and has the following beneficial effects:

1. According to the femoral artery cannula for providing lower limb blood perfusion, by receiving the liquid injection tube in the cannula in a normal state, the liquid injection tube can be protected from contamination as much as possible, and by rotating the worm to drive the worm wheel to rotate, the rotary rod can drive the cam to rotate, that is, the liquid injection tube can be pushed out of the cannula, which is convenient to use.

2. According to the femoral artery cannula for providing lower limb blood perfusion, by providing a blocking plate against the outer wall of the through slot, an interior of the cannula can be blocked and protected in a normal state, so that foreign bodies can be effectively prevented from entering the cannula.

The parts not involved in the apparatus are the same as those in the existing technology or can be implemented by using the existing technology, and according to the present invention, the liquid injection tube can be received in the cannula and taken out when used, so that the liquid injection tube can be protected from contamination as much as possible.

Figure 1:
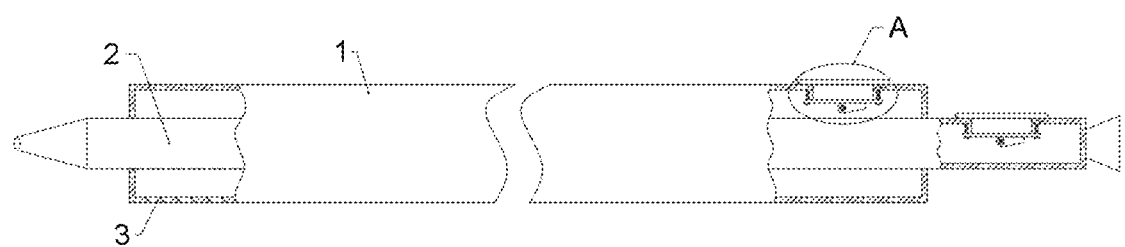
FIG. 1 is a schematic diagram of a structure a femoral artery cannula for providing lower limb blood perfusion according to the present invention.

In the drawings: 1. outer tube, 2. inner tube, 3. through hole, 4. sliding rod, 5 sliding plate, 6. liquid injection tube, 7. rotary rod, 8. cam, 9. worm wheel, 10. side plate, 11. worm, 12. rotary wheel, 13. spring, 14. stopper, 15. blocking plate, 16. connecting strip, and 17. engaging block.

DETAILED DESCRIPTION

The following clearly and completely describes the technical solutions in the embodiments of the present invention with reference to the accompanying drawings in the embodiments of the present invention. Apparently, the described embodiments are some of the embodiments of the present invention rather than all of the embodiments.

In the description of the present invention, it should be understood that orientation or position relationships indicated by the terms such as "on", "below", "front", "back", "left", "right", "top", "bottom", "inner", and "outer" are based on orientation or position relationships shown in the accompanying drawings, and are used only for ease and brevity of illustration and description, rather than indicating or implying that the mentioned apparatus or component needs to have a particular orientation or need to be constructed and operated in a particular orientation. Therefore, such terms should not be construed as limiting of the present invention.

Figure 2:
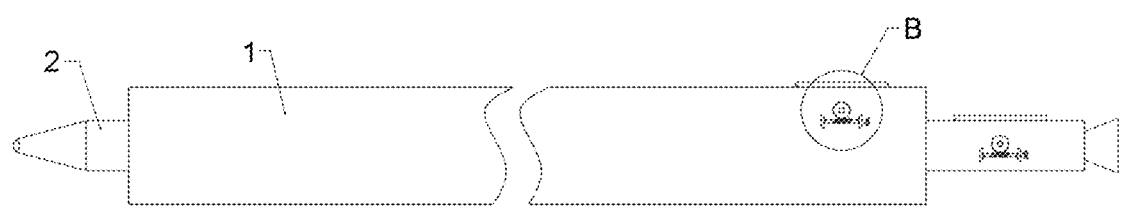
FIG. 2 is a schematic diagram of an integral structure of FIG. 1.
Figure 3:
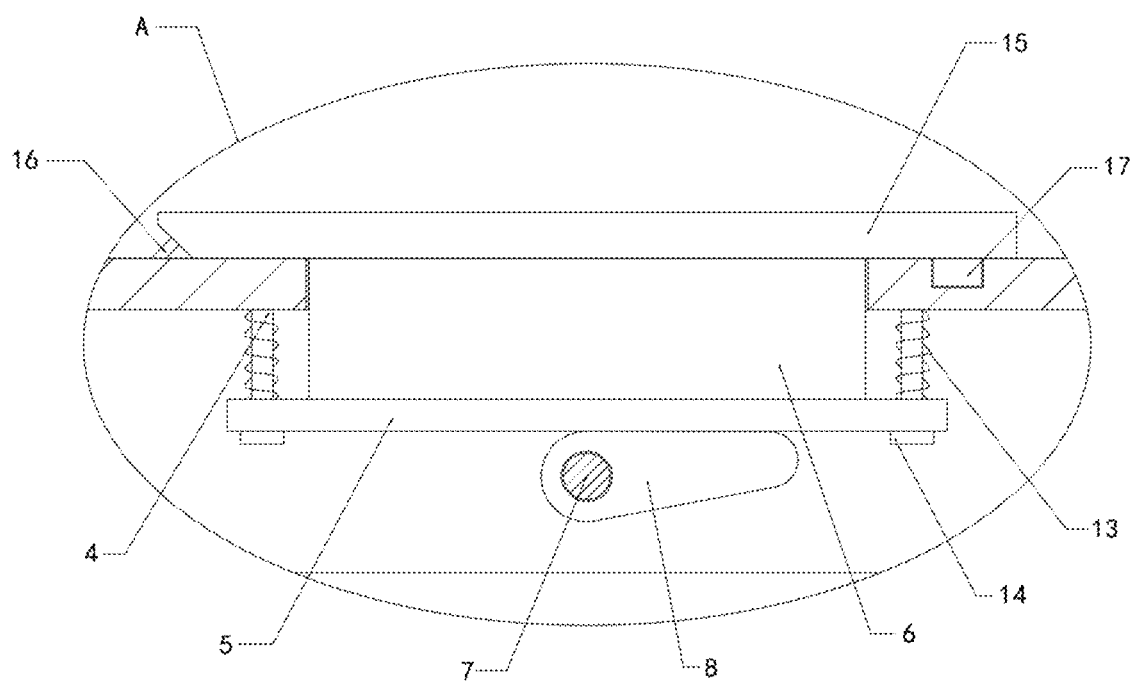
FIG. 3 is a schematic structurally enlarged diagram of portion A in FIG. 1.
Figure 4:
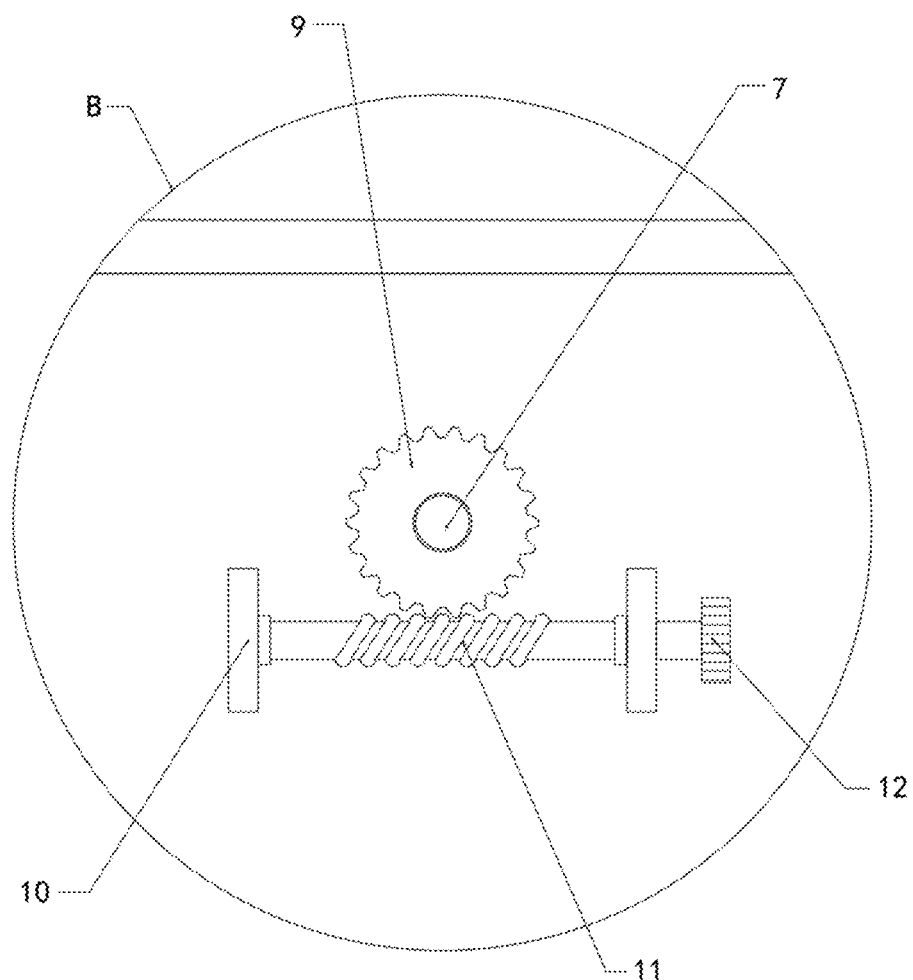
FIG. 4 is a schematic structurally enlarged diagram of portion B in FIG. 2.

Referring to FIG. 1 to FIG. 4, provided is a femoral artery cannula for providing lower limb blood perfusion, including an outer tube 1 and an inner tube 2. The inner tube 2 is fixedly nested inside the outer tube 1, a lower surface of the outer tube 1 is provided with a plurality of through holes 3, upper surfaces of outer sides of the outer tube 1 and the inner tube 2 are each provided with a through slot, two ends of lower sides of the two through slots are each fixedly provided with a sliding rod 4, a sliding plate 5 is connected between the two sliding rods 4 in a movably adjustable manner, a liquid injection tube 6 is fixedly nested in an inner side of the sliding plate 5, lower sides of the two sliding plates 5 are each provided with a transmission mechanism for pushing the liquid injection tubes 6 to move, and outer sides of the through slots are each provided with a blocking mechanism.

The transmission mechanism includes a rotary rod 7 and a cam 8, the rotary rod 7 is arranged on the lower side of the sliding plate 5, two ends of the rotary rods 7 are rotatably connected to side walls of the corresponding outer tube 1 and inner tube 2 through sealed bearings, the cam 8 is fixedly nested on an outer wall of the rotary rod 7, the cam 8 abuts against a lower surface of the sliding plate 5, one ends of the two rotary rods 7 respectively extend to outer sides of the corresponding outer tube 1 and inner tube 2 and are each fixedly nested with a worm wheel 9, one side of the worm wheel 9 is meshed with a worm 11, two ends of the worm 11 are each rotatably connected to a side plate 10, and the plurality of side plates 10 are respectively fixedly connected to the outer walls of the corresponding outer tube 1 and inner tube 2.

The blocking mechanism includes a blocking plate 15 and an engaging block 17, the blocking plate 15 is arranged against the outer side of the through slot, one ends of the two blocking plates 15 are fixedly connected to outer walls of the corresponding outer tube 1 and inner tube 2 through connecting strips 16, the engaging block 17 is fixedly arranged on an end of the corresponding blocking plate 15 away from the connecting strip 16, and the outer walls of the outer tube 1 and the inner tube 2 close to the engaging blocks 17 are each provided with an engaging slot, and the engaging blocks 17 are engaged with the corresponding engaging slots.

Rod walls of the plurality of sliding rods 4 are all movably sleeved with springs 13, and two ends of the plurality of springs 13 are fixedly connected to the corresponding sliding plate 5 and outer walls of the corresponding outer tube 1 and inner tube 2, so that the sliding plates 5 can drive the liquid injection tubes 6 to reset and retract into the cannula.

Lower ends of the plurality of sliding rods 4 are fixedly provided with stoppers 14, to prevent the sliding plates 5 from slipping off the rod walls of the sliding rods 4 as much as possible. One ends of the two worms 11 are each fixedly nested with a rotary wheel 12, to facilitate rotation of the worms 11.

The blocking plates 15, the connecting strips 16, and the engaging blocks 17 are all made of an antibacterial silica gel material, which is convenient to open and has good antibacterial performance.

In the present invention, during use, the liquid injection tube 6 is received in the cannula in a normal state, and therefore, the liquid injection tube can be protected from contamination as much as possible; the outer walls of the through slots are each provided with the blocking plate 15, an interior of the cannula can be blocked and protected in the normal state, so that foreign matters can be effectively prevented from entering the cannula; when connection is required, the worm 11 is rotated to drive the worm wheel 9 to rotate, and then the rotary rod 7 can drive the cam 8 to rotate, so that the liquid injection tube 6 can be pushed out of the cannula; the connection is facilitated; after being connected to the external blood transfusion tube, the inner tube 2 transfuses blood to a proximal end of the femoral artery, and the through hole on the side wall of the outer tube 1 transfuses blood to a distal end of the femoral artery, so that the blood is injected into the lower limbs to prevent lower limb ischemia.

The foregoing descriptions are only preferred embodiments of the present invention, but the scope of protection of the present invention is not limited thereto. Any equivalent replacement or modification made by those skilled in the art according to the technical solution and the inventive concept of the present invention within the technical scope disclosed by the present invention should be fall within the scope of protection of the present invention.

What is claimed is:

1. A femoral artery cannula for providing lower limb blood perfusion, comprising an outer tube and an inner tube, wherein the inner tube is fixedly nested inside the outer tube, a lower surface of the outer tube is provided with a plurality of through holes, upper surfaces of outer sides of the outer tube and the inner tube are each provided with a through slot, two ends of lower sides of the two through slots are each fixedly provided with a sliding rod, a sliding plate is connected between the two sliding rods in a movably adjustable manner, a liquid injection tube is fixedly nested in an inner side of the sliding plate, lower sides of the two sliding plates are each provided with a transmission mechanism for pushing the liquid injection tubes to move, and outer sides of the through slots are each provided with a blocking mechanism.

2. The femoral artery cannula for providing lower limb blood perfusion according to claim 1, wherein the transmission mechanism comprises a rotary rod and a cam, the rotary rod is arranged on the lower side of the sliding plate, two ends of the rotary rods are rotatably connected to side walls of the corresponding outer tube and inner tube through sealed bearings, the cam is fixedly nested on an outer wall of the rotary rod, the cam abuts against a lower surface of the sliding plate, one ends of the two rotary rods respectively extend to outer sides of the corresponding outer tube and inner tube and are each fixedly nested with a worm wheel, one side of the worm wheel is meshed with a worm, two ends of the worm are each rotatably connected to a side plate, and the plurality of side plates are respectively fixedly connected to outer walls of the corresponding outer tube and inner tube.

3. The femoral artery cannula for providing lower limb blood perfusion according to claim 1, wherein the blocking mechanism comprises a blocking plate and an engaging block, the blocking plate is arranged against the outer side of the through slot, one ends of the two blocking plates are fixedly connected to outer walls of the corresponding outer tube and inner tube through connecting strips, the engaging block is fixedly arranged on an end of the corresponding blocking plate away from the connecting strip, and the outer walls of the outer tube and the inner tube close to the engaging blocks are each provided with an engaging slot, and the engaging blocks are engaged with the corresponding engaging slots.

4. The femoral artery cannula for providing lower limb blood perfusion according to claim 1, wherein rod walls of the plurality of sliding rods are all movably nested with springs, and two ends of the plurality of springs are fixedly connected to the corresponding sliding plates and outer walls of the outer tube and inner tube, respectively.

5. The femoral artery cannula for providing lower limb blood perfusion according to claim 1, wherein lower ends of the plurality of sliding rods are each fixedly provided with a stopper.

6. The femoral artery cannula for providing lower limb blood perfusion according to claim 2, wherein one ends of the two worms are each fixedly nested with a rotary wheel.

7. The femoral artery cannula for providing lower limb blood perfusion according to claim 3, wherein the blocking plates, the connecting strips, and the engaging blocks are all made of an antibacterial silica gel material.

* * * * *